United States Patent
Mueller et al.

(10) Patent No.: US 7,342,061 B2
(45) Date of Patent: Mar. 11, 2008

(54) METHOD FOR PRODUCING ORGANIC COMPOUNDS CONTAINING POLY-DOPO, AND THE USE OF THE SAME

(75) Inventors: Wolfgang Mueller, Rudolstadt (DE); Erich Meusel, Katzhuette (DE); Klaus Heinemann, Rudolstadt (DE); Eberhard Taeger, Weissbach ueber Rudolstadt (DE)

(73) Assignee: Thueringisches Institut fr Textil-und Kunststoff-Forschung e.V., Rudolstadt (DE)

( * ) Notice: Subject to any disclaimer, the term of this patent is extended or adjusted under 35 U.S.C. 154(b) by 162 days.

(21) Appl. No.: 10/558,997

(22) PCT Filed: Jun. 18, 2003

(86) PCT No.: PCT/DE03/02030

§ 371 (c)(1),
(2), (4) Date: Dec. 1, 2005

(87) PCT Pub. No.: WO2004/113355

PCT Pub. Date: Dec. 29, 2004

(65) Prior Publication Data

US 2006/0247344 A1    Nov. 2, 2006

(51) Int. Cl.
*C08J 5/15* (2006.01)
*C08K 5/49* (2006.01)
*C08L 5/49* (2006.01)

(52) U.S. Cl. .................................. 524/121; 556/174

(58) Field of Classification Search ................ 524/121, 524/171

See application file for complete search history.

(56) References Cited

FOREIGN PATENT DOCUMENTS

| CN | 1339538 | * | 3/2002 |
|---|---|---|---|
| DE | 26 46 218 A1 | | 4/1977 |
| DE | 195 22 876 C1 | | 11/1996 |
| DE | 199 33 932 | | 1/2001 |
| EP | 0 806 429 | | 11/1997 |
| EP | 0 806 429 A2 | | 11/1997 |
| EP | 1 090 922 A | | 4/2001 |
| JP | 01284521 | * | 11/1989 |

OTHER PUBLICATIONS

Organikum, 4th edition, VEB Deutscher Verlag der Wissenschaften Berlin 1964, p. 223.
Methods of Organic Chemistry 4th edition, Georg Thieme Verlag Stuttgart, 1977, vol. 5/2a, p. 725.
Lin, Wu and Wang, Journal of Applied Polymer Science 78., 2000, pp. 228-235.

* cited by examiner

*Primary Examiner*—Yvonne (Bonnie) Eyler
*Assistant Examiner*—Chukwuma O. Nwaonicha
(74) *Attorney, Agent, or Firm*—ProPat, L.L.C.

(57) ABSTRACT

The invention relates to a method for producing novel reactive organic compounds containing poly-DOPO and having a higher phosphorus content than known comparable DOPO (9,10-dihydro-9-oxa-10-phospha-phenenthrene-10-oxide) adducts, and to the use thereof for flameproofing thermoplastic polymers, such as polyesters and polyamides. The same flameproofing effect is achieved with smaller additive quantities than previously, thus reducing the influence of the physical, especially textile-physical properties of the polymers. The adducts containing poly-DOPO are formed by reacting DOPO with acetylenes carrying reactive groups, in the presence of a catalyst.

10 Claims, No Drawings

METHOD FOR PRODUCING ORGANIC COMPOUNDS CONTAINING POLY-DOPO, AND THE USE OF THE SAME

CROSS REFERENCE TO RELATED APPLICATIONS

This application is being filed under Rule 1.371 as a national stage application of International Application No. PCT/DE2003/002030 filed Jun. 18, 2003. The International Application PCT/DE2003/002030, is hereby incorporated by reference herein in its entirety.

FIELD OF THE INVENTION

The invention relates to a method for producing novel reactive organic compounds containing poly-DOPO which have a higher phosphorus content than comparable DOPO adducts known hitherto, and to the use of the same for flameproofing thermoplastic polymers, preferably polyesters and polyamides; the amounts added to achieve the same flame retardancy effect are lower than previously customary, thus reducing the influence of the physical, especially textile-physical, properties of the polymers. The adducts containing poly-DOPO are formed by reacting DOPO with acetylenes carrying reactive groups or ester groups.

BACKGROUND OF THE INVENTION

The literature discloses the production of 9,10-dihydro-9-oxa-10-phosphaphenanthrene-10-oxide (referred to in the inventive specification as DOPO) and a number of its derivatives. For example, SAITO describes, in DOS 20 34 887, the production of DOPO and various DOPO derivatives. DE 26 46 218 deals with the reaction of DOPO with itaconic acid and itaconic anhydride, and further modifications of these adducts. ENDO et al. establish in this connection that adducts of DOPO with maleic acid and maleic anhydride, and esters which can be produced therefrom are unsuitable for copolymerizations due to an inadequate degree of esterification of the carboxyl groups of the adducts. DIETRICH et al. also restrict themselves, in DE 195 22 876, to the production of, inter alia, DOPO and DOPO derivatives and reaction products thereof with itaconic acid or itaconic acid compounds, and the use thereof for flameproofing polyester fibers. DOPO derivatives which are obtained specifically by reaction with epichlorohydrin are described by UTZ and SPRENGER in EP 0 806 429. These products are intended to be used for incorporation in epoxy resins. The flameproofing of epoxy resins is also the theme of the paper by LIN, WU and WANG (J. APPL. Polym. Sci. 78, 2000, pp. 228-235). To produce the epoxy resins, they use DOPO adducts with maleic acid and with itaconic acid and react these with diglycidyl or bisphenol A. In EP 1 090 922, TAKEUCHI et al. deal with the production of DOPO from o-phenyl-phenol and of DOPO derivatives with α,β-unsaturated carboxylic acids, and the esters, diols etc. thereof, which are always used together with compounds of divalent metals, preferably zinc, for incorporation in polyesters. This is said to suppress the oxidation of the antimony catalysts during the production of flameproofed polyesters.

It is common to all of these specified methods for producing DOPO derivatives that they use exclusively olefinically unsaturated compounds as reactants during the formation of adducts of DOPO. The number of DOPO molecules which can be added per double bond and thus generally per olefin molecule is therefore limited to one. Exceptions would be dienes or polyenes with correspondingly longer carbon chains, but these are not known from any of the protected rights or literature references. This gives rise to the disadvantage that the phosphorus content of these organic phosphorus compounds has an upper limit, meaning that a relatively high minimum amount of flame retardant as comonomer is required in order to achieve a certain flame retardancy effect on incorporating these flame retardants into polymers. This in turn results in an unfavorable effect on the properties of the copolymers formed.

SUMMARY OF ADVANTAGEOUS EMBODIMENTS OF THE INVENTION

An object of the invention is therefore to develop a method for producing reactive organic compounds containing poly-DOPO and having a higher phosphorus content than has hitherto been achievable on the basis of DOPO derivatives, which are suitable for serving as comonomers for flameproofing thermoplastic polymers, such as, for example, polyesters and polyamides.

DETAILED DESCRIPTION OF ADVANTAGEOUS EMBODIMENTS OF THE INVENTION

This aim is achieved surprisingly and according to the invention through obtaining these by addition of 9,10-dihydro-9-oxa-10-phosphaphenanthrene-10-oxide (DOPO) onto acetylenically unsaturated compounds which carry reactive groups, in the presence of a catalyst which is suitable for the addition of triple bonds. Catalysts customary for the addition of triple bonds may be mercury salts or copper salts or amines, such as triethylamine or of catalysts which are not characteristic of this type of reaction, such as, for example, aluminum triisopropoxide. When an appropriate molar ratio of DOPO to the acetylenically unsaturated compound is used, such as 1.5/1 to 3/1, preferably 1.9/1 to 2.1/1, two mol of DOPO are added per mole of the acetylenically unsaturated compound while sacrificing the C≡C triple bond.

This produces an adduct of the following general structure:

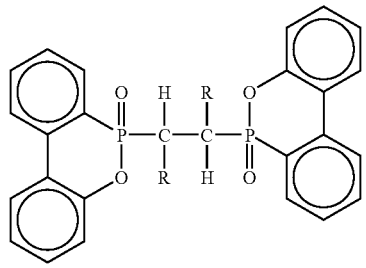

where R may be carboxyl, carboxyalkyl, carboxyaryl, hydroxyalkyl, alkoxyalkyl, aroxyalkyl, hydroxyaryl, alkoxyaryl, aroxyaryl or analogous groups and may be identical or different substituents.

The addition reaction is preferably carried out in solution. Suitable solvents are, particularly, those which are able to dissolve the starting materials, but not the reaction product. Such a solvent is, for example, 1,4-dioxane.

According to the literature (Organikum, 4th edition, VEB Deutscher Verlag der Wissenschaften Berlin 1964, p. 223), the electrophilic addition of H-acidic compounds onto acetylenes proceeds only in the presence of specific catalysts, such as mercury salts and copper salts since the acetylene bond is relatively unreactive toward electrophilic reagents. According to Houben-Weyl (Methoden der organischen Chemie [Methods of organic chemistry] 4th edition, Georg Thieme Verlag Stuttgart, 1977, volume 5/2a, p. 725), the presence of amines as catalysts is required for the nucleophilic addition of phosphines onto C≡C triple bonds. According to the invention, it has now been found that the addition reaction of DOPO onto certain acetylenes can also be catalyzed by compounds such as aluminum triisopropoxide. The catalyst used for the reaction of the organophosphorous compound DOPO with the acetylenically unsaturated compound is mercury salts or copper salts or amines or, preferably, aluminum triisopropoxide. This variant of a reaction of DOPO onto unsaturated compounds is hitherto not known.

The acetylenically unsaturated compounds used are, for example, substances such as 2-butyne-1,4-diol diacetate, 2-butyne-1,4-diol, 3-hexyne-2,5-diol, 2,4-hexadiyne-1,6-diol and esters thereof, and preferably acetylenedicarboxylic acid and acetylenedicarboxylic diesters.

The resulting DOPO adducts with phosphorous contents up to 12.7% are used as comonomers in polyester condensation in amounts of from 1 to 15%. DOPO adducts with hydroxyl end groups do not necessarily here require a further derivatization. DOPO adducts of the acetylenedicarboxylic acid and of the acetylenedicarboxylic diesters are advantageously converted into diglycol esters prior to being used as comonomers.

The DOPO/acetylenedicarboxylic acid adducts, and to a lesser extent their derivatives, exhibit decarboxylation at temperatures of about 200° C. and above. It has proven to be advantageous to meter in the DOPO adducts into a polycondensation mixture which is already precondensed. The catalysts used for the polyester polycondensation are the products known from the prior art, such as, for example, antimony trioxide, antimony acetate or tetra-n-butyl orthotitanate.

In order to convert the addition compounds into a form suitable as comonomers particularly for copolyamides, further derivatizations, such as the formation of carboxaminoamides or carboxylic/amine salts are used. For this, the DOPO/dicarboxylic acid adducts are reacted with the corresponding equimolar amount of a diamine similarly to the formation of AH salt and used as comonomers in the preparation of polyamides. The amount added is governed by the phosphorus content which is desired in the copolyamide. It ranges between 3 and 20%, preferably between 5 and 15%. Besides the DOPO/acetylenedicarboxylic acid adducts, DOPO/maleic acid adducts are also in principle likewise suitable.

EXAMPLES

Example 1

108 g of DOPO and 1 g of aluminum triisopropoxide are dissolved in 700 ml of dioxane at about 30° C. A solution of 22.8 g of acetylenedicarboxylic acid in 80 ml of dioxane and 40 ml of diethyl ether, which has been prepared with gentle heating, is added dropwise, with stirring, to the clear solution. When the addition is complete, the temperature is increased to 50-60° C. The treatment is continued over about 20 hours. The precipitate which gradually forms is separated off from the supernatant solution by filtration. After the solvent residues have been removed, a white, pulverulent product is obtained in a yield, based on the acetylenedicarboxylic acid used, of 94.5%. The product (empirical formula: $C_{28}H_{20}O_8P_2$) has a phosphorus content of 10.9% (theoretical value: 11.3%). The carboxyl group content is 2777 μequ/g. The product has a melting point of 199° C., with decarboxylation taking place directly after the melting process.

Example 2

162 g of DOPO and 1.2 g of mercury(II) sulfate are dissolved in 600 ml of dioxane at about 30° C. A solution of 21.5 g of 2-butyne-1,4-diol in 100 ml of dioxane is added dropwise, with stirring, to the slightly milky solution. When the addition is complete, the temperature is increased to 50-60° C. The treatment is continued over about 20 hours. Following the distillative removal of the solvent and of the unreacted butynediol, a yellowish product is obtained. The product (empirical formula: $C_{28}H_{24}O_6P_2$), following extraction with diisopropyl ether, has a phosphorus content of 11.5% (theoretical value: 11.95%). The product has a melting point of 105° C.

Example 3

86.4 g of DOPO and 1.0 g of triethylamine are dissolved in 700 ml of dioxane at about 30° C. A solution of 21.3 g of acetylenedicarboxylic dimethyl ester in 100 ml of dioxane is added dropwise, with stirring, to the clear solution. When the addition is complete, the temperature is increased gradually to 96-98° C. The reaction is continued over about 10 hours. The precipitate which forms is separated off from the supernatant solution by filtration after standing overnight. Following the removal of the solvent residues, a white product is obtained in a yield, based on the acetylenedicarboxylic dimethyl ester used, of 87.9%. The product (empirical formula: $C_{30}H_{24}O_8P_2$) has a phosphorus content of 10.7% (theoretical value: 10.79%). The product has a melting point of 281.6° C. (DCS). A decarboxylation in the form established for the DOPO/acetylenedicarboxylic acid adduct from Example 1 does not occur here.

Example 4

54.6 g of DOPO/acetylenedicarboxylic acid adduct from Example 1 are suspended together with 1 g of p-toluenesulfonic acid and 60 g of ethylene glycol in 100 ml of dioxane. The mixture is treated for 16 hours at 100° C. The white precipitate which settles out is separated off from the supernatant solution by filtration. Residues of solvent and ethylene glycol are removed by vacuum distillation. The white pulverulent product is obtained in a yield, based on the DOPO/acetylenedicarboxylic acid adduct used, of 68.5%. The product (empirical formula: $C_{32}H_{28}O_{10}P_2$) is to be described as DOPO/acetylenedicarboxylic acid diglycol ester adduct and has a phosphorus content of 10.1% (theoretical value: 9.8%)

Example 5

54.6 g of DOPO/acetylenedicarboxylic acid adduct from Example 1 are dissolved in 260 ml of freshly distilled dimethylacetamide with heating. 23.2 g of a 50% strength solution of 1,6-diaminohexane in dimethylacetamide are added dropwise to this solution. Approximately 30 minutes after the addition is complete, the heating source is removed. Upon cooling the reaction mixture to room temperature, a white precipitate is formed. This is separated off by filtration, and washed with dimethylacetamide and then with ethanol. The product is then dried in a vacuum drying cabinet at 80° C.

Example 6

96.6 g of terephthalic acid diglycol ester are mixed with 0.1 g of tetra-n-butyl orthotitanate and used in a bath at 200° C. with the gentle introduction of nitrogen. The bath temperature is increased to 270° C. over the course of 60 minutes. With continuous stirring, distillation of the ethylene glycol starts, which is a sure sign of the onset of condensation. Distillation is aided by applying a slight vacuum. After about 40% of the ethylene glycol which is to be expected in theory has distilled off, 12.7 g of a DOPO/acetylenedicarboxylic acid diglycol ester adduct are added with vigorous stirring. The ethylene glycol distillation and thus the polycondensation is continued under vacuum. After about 120 minutes, the temperature is increased to 280° C. at a vacuum of <1 mbar. The polycondensation is continued under these conditions for about a further 30 minutes. The very viscous melt is then poured out. The resulting modified polyester melts at 229-231° C. The relative solution viscosity was determined as 1.26. The product shows a carboxyl group content of 63 µequ/g and a phosphorus content of 1.58%.

Example 7

84 g of ε-caprolactam are mixed with 16 g of the product from Example 5 and 1 ml of water and flushed thoroughly with nitrogen. The vessel containing the reaction mixture is placed into a bath at a temperature of 200° C. After the mixture has melted, it is stirred vigorously. The temperature is gradually increased to 260° C. and the polymerization is continued with a constant introduction of a small amount of nitrogen over about 14 hours. A copolyamide with a relative solution viscosity of 1.45 is formed. Following water extraction under reflux, a copolyamide with a solution viscosity slightly increased to 1.47 is obtained. The carboxyl group content is 64.5 µequ/g, the amino group content 50.2 µequ/g. The product has a phosphorus content of 1.5% compared with a value before extraction of 1.38%. It melts at 214° C.

Example 8

96.6 g of terephthalic acid diglycol ester are mixed with 10.4 g of the DOPO/butynediol adduct from Example 2 and 0.1 g of tetra-n-butyl orthotitanate and used in a bath at 200° C. with the gentle introduction of nitrogen. The bath temperature is increased to 270° C. over the course of 60 minutes. With continuous stirring, ethylene glycol is then distilled off. The distillation is aided by applying a gentle vacuum. The polycondensation is continued under vacuum, which is gradually increased to about 1 mbar. After about 120 minutes, the temperature is increased to 280° C. at a vacuum of <1 mbar. The polycondensation is continued under these conditions for about a further 30 minutes. The very viscous melt is then poured out. The resulting modified polyester melts at 232-234° C. The relative solution viscosity was determined as 1.22. The product shows a phosphorus content of 1.47%.

The invention claimed is:

1. A method for producing reactive organic compounds containing poly-DOPO, said method comprising reacting 9,10-dihydro-9-oxa-10-phosphaphenanthrene-10-oxide (DOPO) with acetylenically unsaturated compounds having reactive groups, wherein said reacting step is performed in the presence of a catalyst which is suitable for the addition of triple bonds.

2. The method as claimed in claim 1, wherein the organophosphorus compound DOPO and the acetylenically unsaturated compound are reacted with one another in a ratio of 1.5 to 3 mol of DOPO per triple bond.

3. The method as claimed in claim 1, wherein the acetylenically unsaturated compounds used are alkynes, alkynols, alkynecarboxylic acids, alkynecarboxylic esters or corresponding alkadiyne compounds.

4. The method as claimed in claim 1, wherein the catalyst used for the reaction of the organophosphorus compound DOPO with the acetylenically unsaturated compound is mercury salts, copper salts, amines or aluminum triisopropoxide.

5. The method as claimed in claim 1, wherein the addition reaction is carried out in solution.

6. Flame retardant thermoplastic polymers comprising the reactive organic compounds containing poly-DOPO prepared as in claim 1.

7. The method as claimed in claim 2, wherein the ratio is 1.9 to 2.1 mol of DOPO per triple bond.

8. The method as claimed in claim 5, wherein the addition reaction is carried out in 1,4-dioxane.

9. A method for producing reactive organic compounds containing poly-DOPO as claimed in claim 1, wherein the reactive groups on the acetylenically unsaturated compounds are acetylenedicarboxylic acid or acetylenedicarboxylic diester, and said method further comprises converting the acetylenedicarboxylic acid or acetylenedicarboxylic diester into diglycol ester or the reactive groups on the acetylenically unsaturated compounds is dicarboxylic acid, and said method further comprises converting the dicarboxylic acid into carboxyaminoamide or carboxylic/amide salt.

10. Flame retardant for thermoplastic polymers comprising the formula

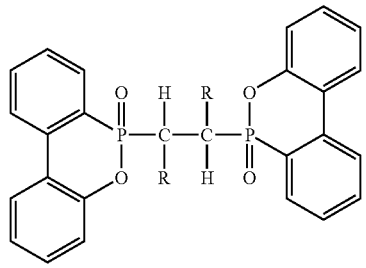

where R is independently selected from carboxyl, carboxyalkyl, carboxyaryl, hydroxyalkyl, alkoxyalkyl, aroxyalkyl, hydroxyaryl, alkoxyaryl or aroxyaryl.

* * * * *